United States Statutory Invention Registration [19]

[11] Reg. Number: H725

Gordon [43] Published: Jan. 2, 1990

[54] UREIDO AMINO AND IMINO ACIDS, COMPOSITIONS AND METHODS FOR USE

[75] Inventor: Eric M. Gordon, Pennington, N.J.

[73] Assignee: E. R. Squibb & Sons, Inc., Princeton, N.J.

[21] Appl. No.: 19,469

[22] Filed: Feb. 26, 1987

[51] Int. Cl.[4] ..... C07D 207/09
[52] U.S. Cl. ..... 548/533
[58] Field of Search ..... 548/533; 514/423

[56] References Cited

U.S. PATENT DOCUMENTS 4,604,402 8/1986 Godfrey, Jr. et al. ..... 514/333
4,621,092 11/1986 Natarajan et al. ..... 514/343

OTHER PUBLICATIONS

Almquist et al., "Synthesis and Biological Activity . . . Angiotensin Converting Enzyme", J. Med. Chem., (1980), 23, pp. 1392–1398.

Almquist et al., "Synthesis and Biological Activity . . . 5(S)–Benzamido–4–oxo–6–phenylhexanoyl–L–proline", J. Med. Chem., 1985, 28, pp. 1062–1066, 1067–1071.

*Primary Examiner*—John F. Terapane
*Assistant Examiner*—Valeria Fee
*Attorney, Agent, or Firm*—Theodore R. Furman, Jr.

[57] ABSTRACT

Compounds of the formula wherein X is various amino or imino acids and esters are disclosed. These compounds are useful due to their angiotensin converting enzyme inhibition activity and depending upon the definition of X may also be useful as analgesics due to their enkephalinase inhibition activity.

6 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

UREIDO AMINO AND IMINO ACIDS, COMPOSITIONS AND METHODS FOR USE

FIELD OF THE INVENTION

The present invention relates to ureido amino and imino acid compounds and more particularly concerns such compounds, compositions including such compounds and methods for their use.

BACKGROUND OF THE INVENTION

Almquist et al., "Synthesis and Biological Activity of a Ketomethylene Analogue of a Tripeptide Inhibitor of Angiotensin Converting Enzyme", *J. Med. Chem.*, 1980, 23, 1392–1398, discloses the ketomethylene compound the formula

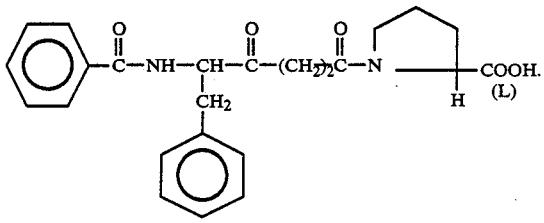

This and related compounds are also disclosed by Almquist et al. in U.S. Pat. No. 4,329,473.

Natarajan et al. in U.S. Pat. No. 4,621,092 disclose compounds of the formula

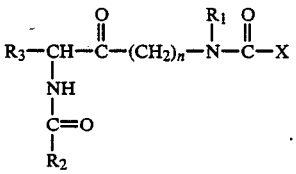

These compounds are useful as hypotensive agents due to their angiotensin converting enzyme inhibition activity and depending upon the definition of X may also be useful as analgesics due to their enkephalinase inhibition activity.

Godfrey, Jr. et al. in U.S. Pat. No. 4,604,402 disclose compounds of the formula

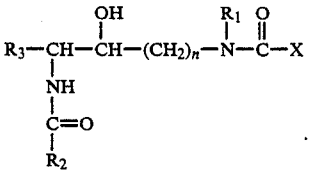

These compounds are useful as hypotensive agents due to their angiotensin converting enzyme inhibition activity and depending upon the definition of X may also be useful as analgesics due to their enkephalinase inhibition activity.

SUMMARY OF THE INVENTION

In accordance with the present invention novel ureido imino and amino acid compounds useful, for example, as hypotensive agents are disclosed. The various ureido-keto and hydroxy-substituted ureido compounds have the general formula

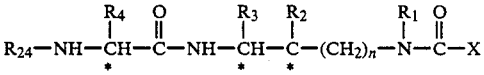

I wherein $R_1$ is hydrogen, lower alkyl, halo substituted lower alkyl,

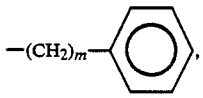

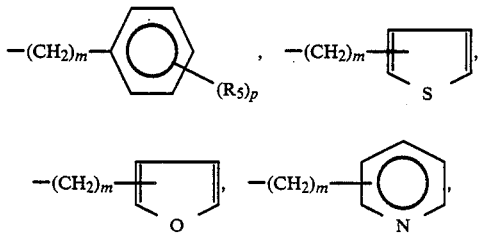

$-(CH_2)_m$—cycloalkyl, $-(CH_2)_2-NH_2$, $-(CH_2)_3-NH_2$, $-(CH_2)_4-NH_2$,

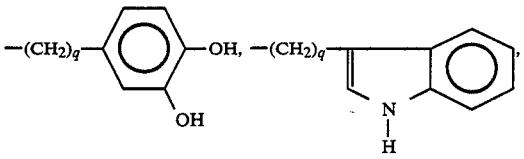

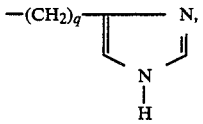

$-(CH_2)_q-SH$, $(CH_2)_q-OH$, $-(CH_2)_q-S-$lower alkyl,

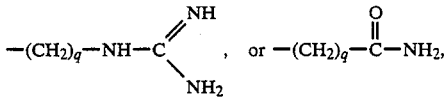

n is one or two, $R_2$ is

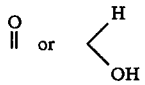

$R_3$ and $R_4$ are independently selected from hydrogen, lower alkyl,

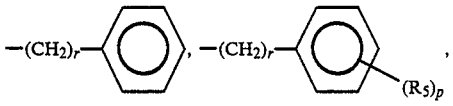

$-(CH_2)_r$—cycloalkyl, $-(CH_2)_r-NH_2$, $-(CH_2)_r-Cl$,

-continued
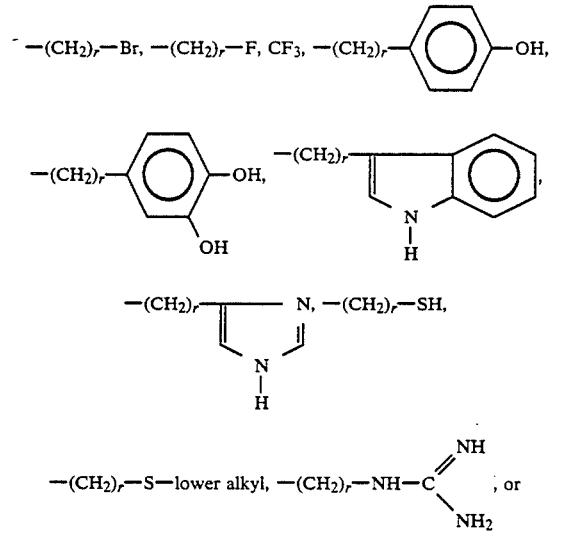
$R_{24}$ is hydrogen,
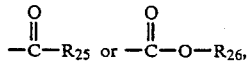
$R_{25}$ is hydrogen, lower alkyl,
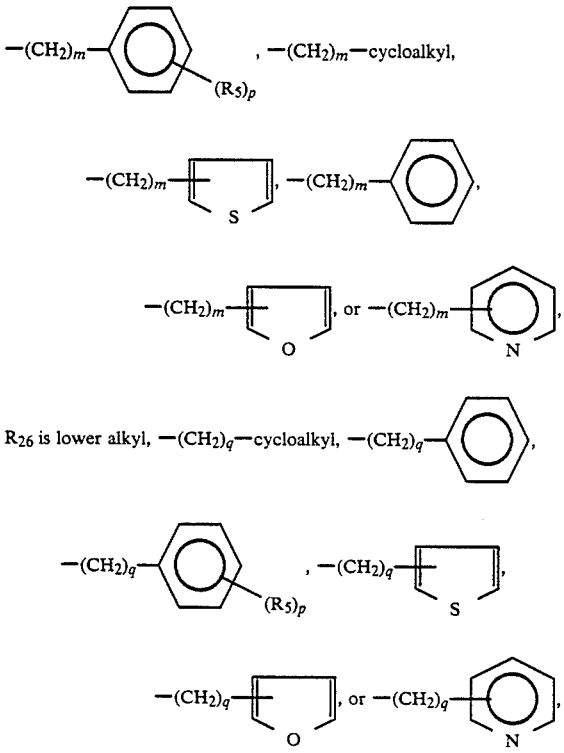
$R_{26}$ is lower alkyl, $-(CH_2)_q-$cycloalkyl, $-(CH_2)_q-$
m is zero or an integer from 1 to 4,
r is an integer from 1 to 7,
q is an integer from 1 to 4,
X is an animo or imino acid or ester of the formula
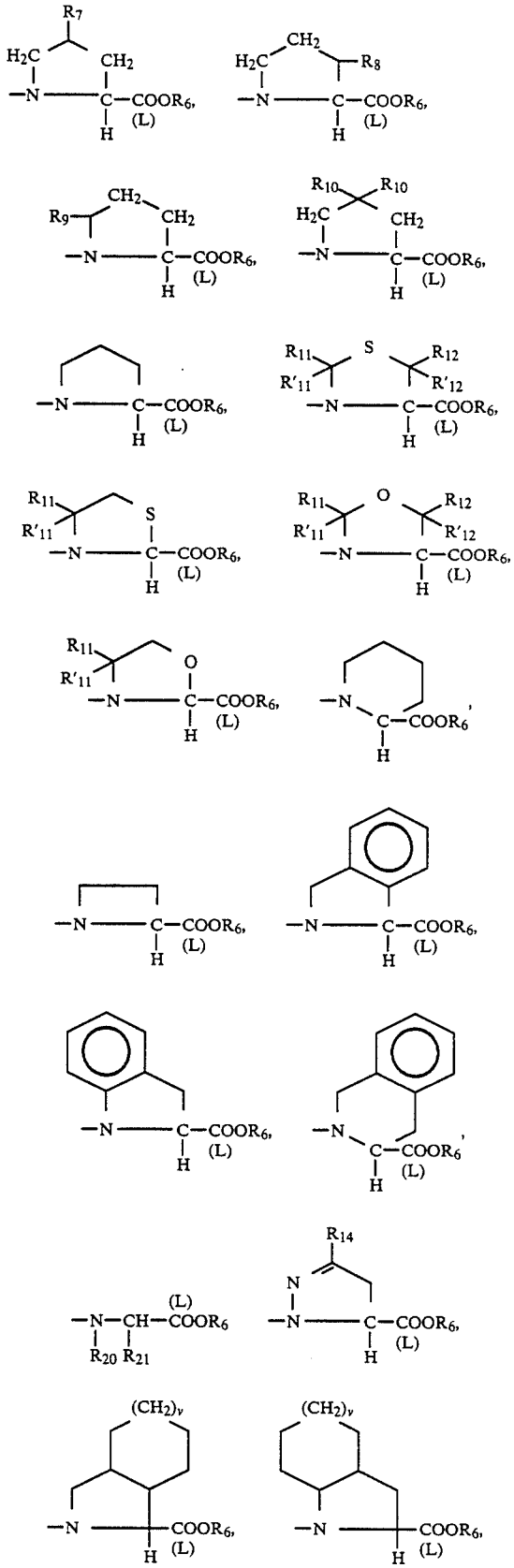

-continued
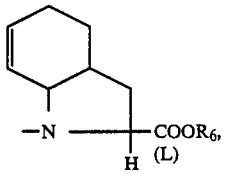
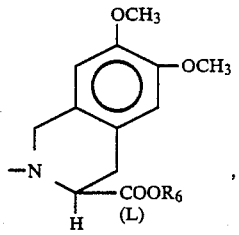
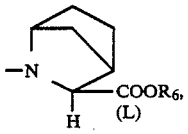
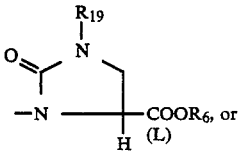
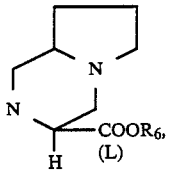
$R_7$ is hydrogen, lower alkyl, halogen, hydroxy,
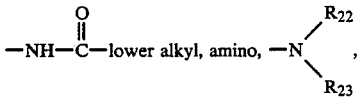
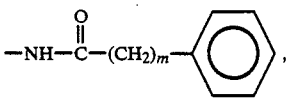
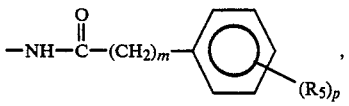
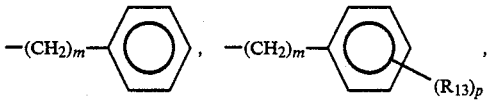
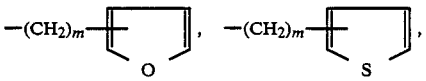
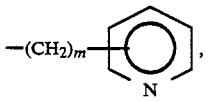
a 1- or 2-naphthyl of the formula
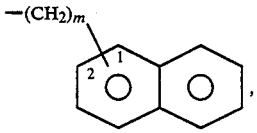
a substituted 1- or 2-naphthyl of the formula
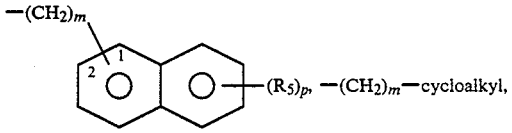
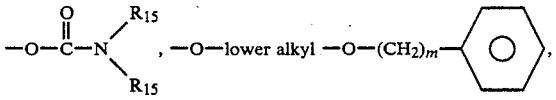
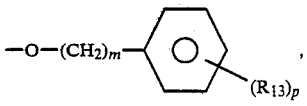
a 1- or 2-naphthyloxy of the formula
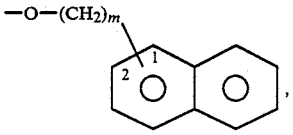
a substituted 1- or 2-naphthyloxy of the formula
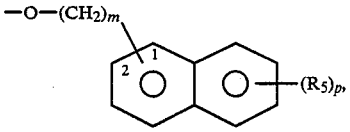
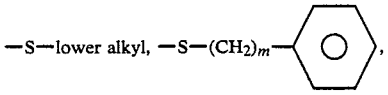
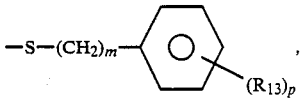
a 1- or 2-naphthylthio of the formula
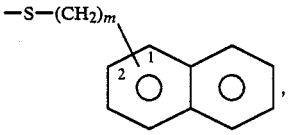
or a substituted 1- or 2-naphthylthio of the formula
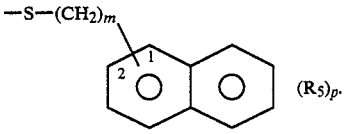
$R_8$ is lower alkyl, halogen,

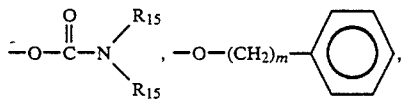

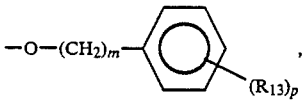

—O—lower alkyl, a 1- or 2-naphthyloxy of the formula

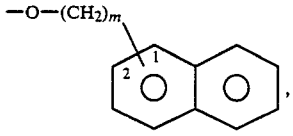

a substituted 1- or 2-naphthyloxy of the formula

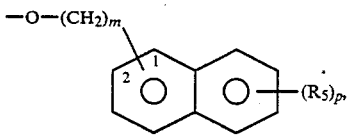

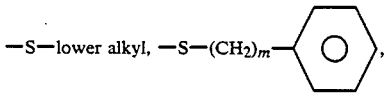

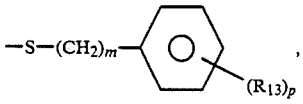

a 1- or 2-naphthylthio of the formula

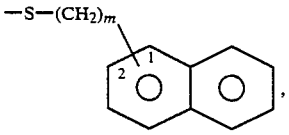

or a substituted 1- or 2-naphthylthio of the formula

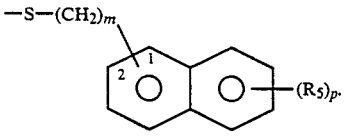

$R_9$ is lower alkyl, keto,

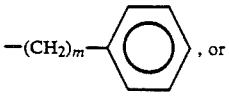

-continued

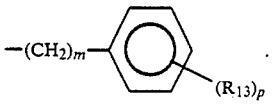

$R_{10}$ is halogen or Y-$R_{16}$.

$R_{11}$, $R'_{11}$, $R_{12}$ or $R'_{12}$ are independently selected from hydrogen and lower alkyl or $R'_{11}$, $R_{12}$ and $R'_{12}$ are hydrogen and $R_{11}$ is

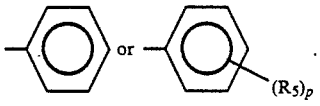

$R_{13}$ is lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenythio, or phenylmethyl.

$R_5$ is lower alkyl of 1 to 4 carbons, lower alkoxy of 1 to 4 carbons, lower alkylthio of 1 to 4 carbons, chlorl, bromo, fluoro, trifluoromethyl or hydroxy.

$R_6$ is hydrogen, lower alkyl, benzyl, benzhydryl, alkali metal salt ion, alkaline earth metal salt ion,

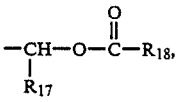

or —$(CH_2)_2Si(CH_3)_3$.

p is one, two or three provided that p is more than one only if $R_{13}$ or $R_5$ is methyl, methoxy, chloro, bromo or fluoro.

$R_{14}$ is hydrogen, lower alkyl,

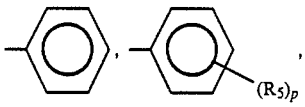

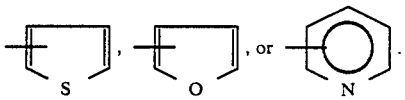

$R_{15}$ is hydrogen or lower alkyl of 1 to 4 carbons.

Y is oxygen or sulfur.

$R_{16}$ is lower alkyl of 1 to 4 carbons,

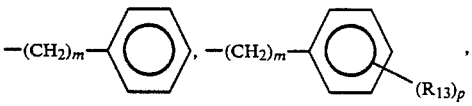

or the $R_{16}$ groups join to complete an unsubstituted 5- or 6-membered ring or said ring in which one or more of the carbons has a lower alkyl of 1 to 4 carbons of a di(lower alkyl of 1 to 4 carbons) substituent.

$R_{17}$ is hydrogen, lower alkyl, cycloalkyl, or phenyl.

$R_{18}$ is hydrogen, lower alkyl, lower alkoxy, or phenyl.

v is zero, one, or two $R_{19}$ is lower alkyl or

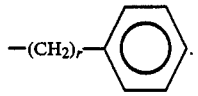

$R_{20}$ is hydrogen, lower alkyl,

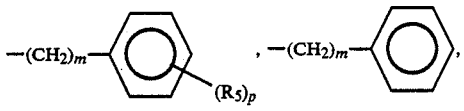

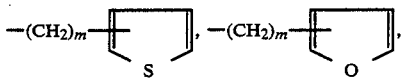

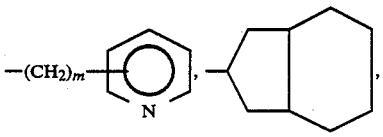

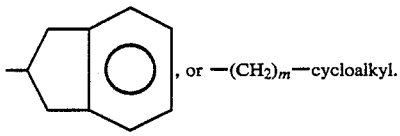

, or $-(CH_2)_m-$cycloalkyl.

$R_{21}$ is hydrogen, lower alkyl,

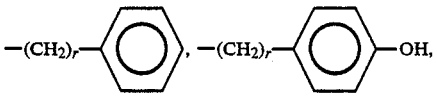

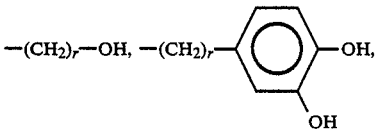

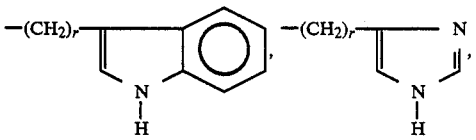

$-(CH_2)_r-NH_2$, $-(CH_2)_r-SH$, $-(CH_2)_r-S-$lower alkyl,

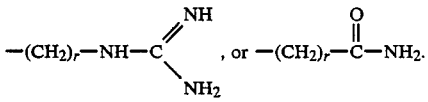

$R_{22}$ is lower alkyl, benzyl, or phenethyl.

$R_{23}$ is hydrogen, lower alkyl, benzyl, or phenethyl.

DETAILED DESCRIPTION OF THE INVENTION

This invention is directed to the various novel ureido-keto and hydroxy-substituted ureido imino and amino acid compounds of formula I above, and compositions and methods of using compositions containing the novel compounds.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkythio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethy, bromomethyl, etc.

The symbols

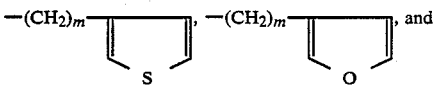

, and

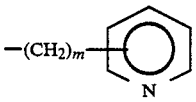

represent that the alkylene bridge is attached to an available carbon atom.

$R_2$ is

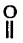

and n=1, a compound of the formula

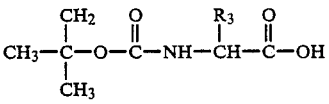

II is reacted with a chlorocarbonate of the formula

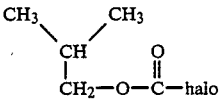

III in the presence of a base, such as triethylamine or diisopropylethylamine followed by diazomethane to provide a compound of the formula

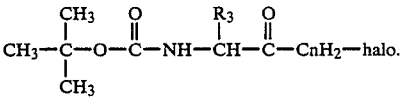

IV

Compound IV is reacted with amine of the formula

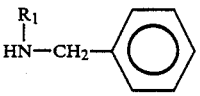

V (the benzyl function acting as a nitrogen protecting group) in the presence of a base such as triethylamine and then treated with p-toluenesulfonic acid (pTSA) to provide

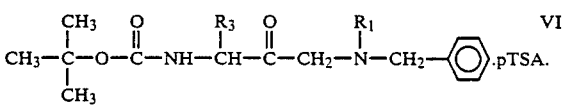

VI

Hydrogenation (for example, by treating with hydrogen in the presence of a palladium on carbon catalyst) to remove the benzyl protecting group yields

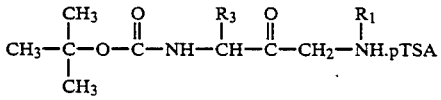

VII which is thereafter reacted with the acid chloride of the formula

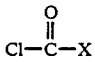

VIII wherein $R_6$ in the definition of X is an easily removable ester protecting group such as benzhydryl or benzyl; in the presence of N-methyl morpholine and an aprotic solvent, e.g. methylene chloride to provide

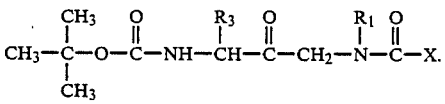

IX

Treatment of compound IX with hydrochloric acid in the presence of an organic solvent, such as ethyl acetate, affords an intermediate of the formula

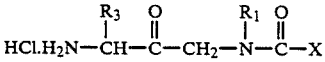

X wherein $R_6$ in the definition of X is still an ester protecting group.

An acid of the formula

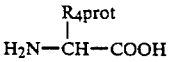

XI (wherein prot is an amino protectin such as benzyloxycarbonyl) is reacted with $R_{24}$—halo (XII)

in the presence of an acid scavenger, e.g. bis(trimethylsilyl)trifluoroacetamide and acetonitrile to provide a compound of the formula

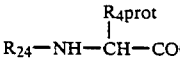

XIII

Compound XIII is thereafter reacted with the compound of formula X in the presence of a base, e.g. triethylamine and a peptide coupling reagent to produce a compound having the formula

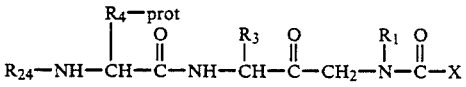

XIV

Compounds of formula I wherein $R_2$ is

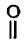

are thereafter obtained by hydrogenation of the compound of formula XIV to remove the protecting groups. For example, hydrogenation with hydrochloric acid in the presence of a palladium on carbon catalyst when Re is benzyl or benzhydryl affords the hydrochloride salt of the compound of formula I wherein $R_2$ is

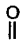

and $R_6$ is hydrogen.

Compounds of formula I wherein $R_2$ is

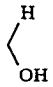

can be obtained by treating compounds of formula I wherein $R_2$ is

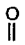

(the preparation of which has been described above) with a conventional reducing agent such as sodium borohydride, sodium cyanoborohydride, diisobutyl aluminum hydride, lithium tri-t-butoxy aluminum hydride and the like.

In the above reactions if any or all of $R_1$, $R_2$ and $R_4$ are

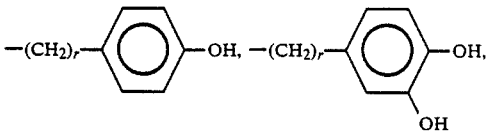

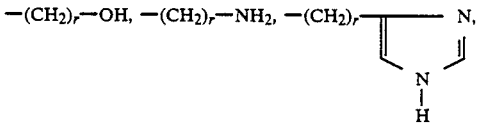

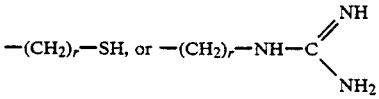

then the hydroxyl, amino, imidazolyl, mercaptan or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction sequence.

The ester products of formula I wherein $R_6$ is lower alkyl, benzyl or benzhydryl can be chemically treated such as with sodium hydroxide in aqueous dioxane or with trimethylsilylbromide to yield the products of formula I wherein $R_6$ is hydrogen. The benzyl and benzhydryl esters can also be hydrogenated, for example by treating with hydrogen in the presence of a palladium on carbon catalyst.

The ester products of formula I wherein $R_6$ is

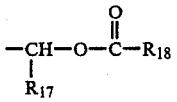

may be obtained by employing the acid chloride of formula VIII in the above reactions with such ester group already in place. Such ester reactants can be prepared by treating the corresponding amino or imino acid of the formula

HX XV wherein $R_6$ is hydrogen with an acid chloride such as

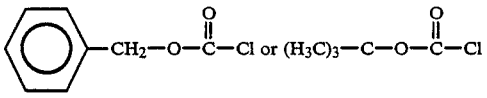

so as to protect the N-atom. The protected amino or imino acid is then reacted in the presence of a base with a compound of the formula

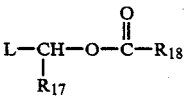

XVI wherein L is a leaving group such as chlorine, bromine, tolylsulfonyl, etc., followed by removal of the N-protecting group such as by treatment with acid or hydrogenation.

The ester products of formula I wherein $R_6$ is

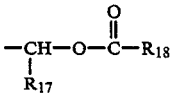

can also be obtained by treating the product of formula I wherein $R_6$ is hydrogen with a molar excess of the compound of formula XVI.

When the compounds of formula I contain a reactive sulfur atom within the amino acid portion of the molecule, i.e. X is

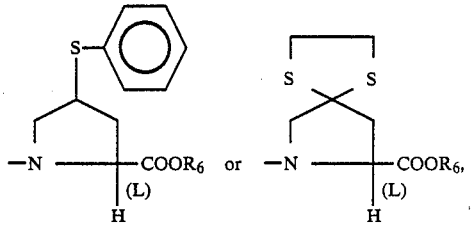

for example, then the above described procedures are somewhat altered to avoid the use of hydrogenation to remove the N-protecting groups. For example, the N-protecting group used should be those which are compatible with acid removal such as benzyloxycarbonyl, t-butyl and the like.

The compounds of formula I wherein $R_6$ is hydrogen form salts with a variety of inorganic or organic bases. The nontoxic, pharmaceutically acceptable salts are preferred, although other salts are also useful in isolating or purifying the product. Such pharmaceutically acceptable salts include metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

Similarly, the compounds of formula I, especially wherein $R_6$ is an ester group, form salts with a variety of inorganic and organic acids. Again, the non-toxic pharmaceutically acceptable salts are preferred, although other salts are also useful in isolating or purifying the product. Such pharmaceutically acceptable salts include those formed with hydrochloric acid, methanesulfonic acid, sulfuric acid, maleic acid, etc. The salts are obtained by reacting the product with an equivalent amount of the acid in a medium in which the salt precipitates.

As shown above, the amino or imino acid portion of the molecule of the products of formula I is in the L-configuration. Several asymmetric centers are also present in the balance of the molecule as represented by the * in formula I. Thus the compounds of formula I can exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_7$, $R_8$ and $R_9$ substituent in the starting material of formula XV.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood, produces angiotensin I. Angiotensin I is converted by angiotensin converting enzyme (ACE to angiotensin II. The latter is an active pressor substance which has been implicated as the causative agent in several forms of hypertension in various mammalian species, e.g. humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g. humans) suffering therefrom is alleviated. A single dose, or preferably two to four divided daily doses, provided on a basis of about 0.1 to 100 mg, preferably about 1 to 50 mg, per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g. chlorothiazide, hydrochlorothiazide, flumethiazide, hydroflumethiazide, bendroflumethiazide, methylchlothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

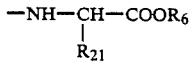

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg per kilogram of body weight per day, preferably about 1 to about 50 mg per kilogram per day, produces the desired analgesic activity. The composition is preferably administered orally but parenteral routes such as subcutaneous can also be employed.

Preferred compounds of this invention with respect to the amino or imino acid part of the structure are those wherein

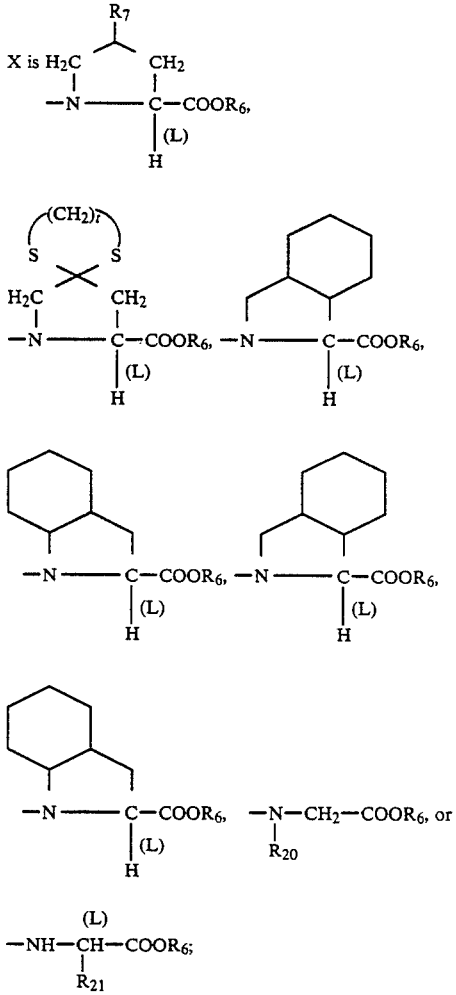

$R_7$ is hydrogen, hydroxy, chloro, fluoro, lower alkyl of 1 to 4 carbons, cyclohexyl, amino, —O-lower alkyl wherein lower alkyl is of 1 to 4 carbons, —S-lower alkyl wherein lower alkyl is of to 4 carbons,

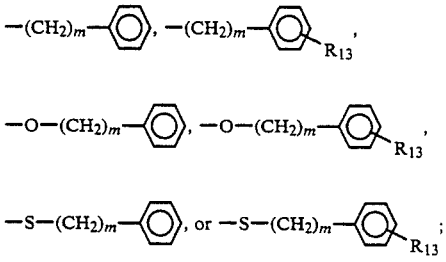

m is zero, one or two.

$R_{13}$ is methyl, methoxy, chloro, fluoro, bromo, methylthio, or hydroxy.

t is 2 or 3.

$R_{21}$ is hydrogen, straight or branched chain lower alkyl of 1 to 4 carbons,

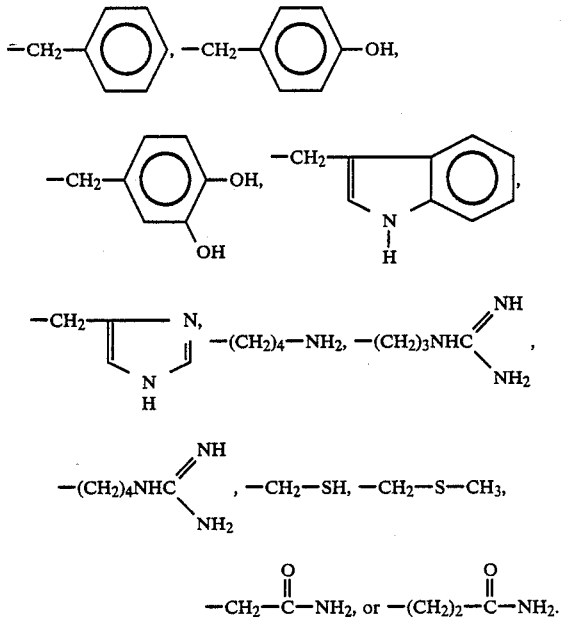

$R_{20}$ is

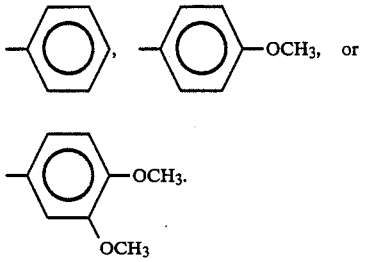

$R_6$ is hydrogen, sodium ion, potassium ion, calcium ion, lithium ion, or

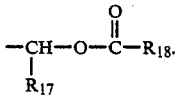

$R_{17}$ is hydrogen, straight or branched chain lower alkyl or 1 to 4 carbons, cyclohexyl, or phenyl.

$R_{18}$ is hydrogen or straight or branched chain lower alkyl of 1 to 4 carbons.

Most preferred are those wherein:

X is

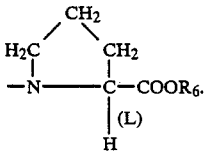

$R_6$ is hydrogen, sodium ion, potassium ion, calcium ion, or lithium ion.

Preferred compounds of this invention with respect to the ureido part of the structure are those wherein $R_1$ is a straight or branched chain lower alkyl of 1 to 4 carbon atoms, $—(CH_2)_r—NH_2$ or

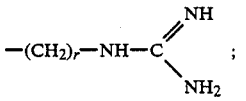

n is 1;

$R_2$ is

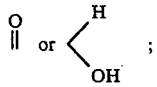

$R_3$ is a branched chain lower alkyl of 1 to 4 carbon atoms,

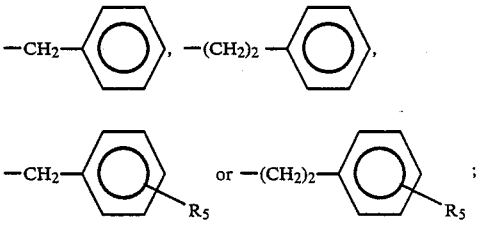

$R_4$ is hydrogen, straight or branched chain lower alkyl of 1 to 4 carbons, $—(CH_2)_r—NH_2$,

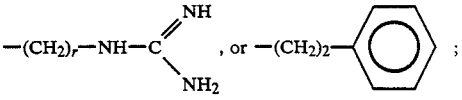

$R_{24}$ is hydrogen,

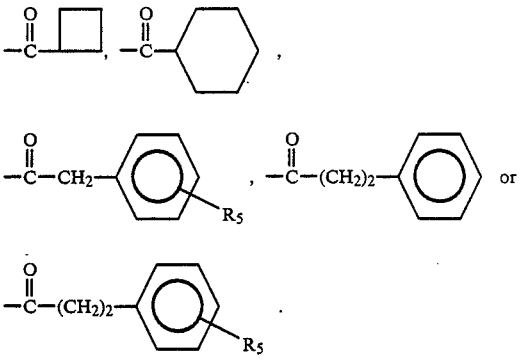

r is an integer from 3 to 5 m is one or two.

$R_5$ is methyl, methoxy, methylthio, chloro, bromo, fluoro, or hydroxy.

$R_{17}$ is hydrogen, straight or branched chain lower alkyl of 1 to 4 carbons, cyclohexyl, or phenyl.

$R_{18}$ a is hydrogen or straight or branched chain lower alkyl of 1 to 4 carbons.

Most preferred are those wherein:

n is one;

$R_1$ is $—CH_3$ or $—(CH_2)_4—NH_2$;

$R_2$ is;

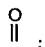

$R_3$ is

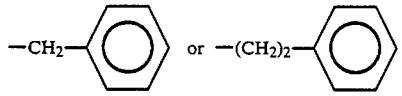

$R_4$ is methyl, n-butyl, or $-(CH_2)_4-NH_2$.
$R_{24}$ is hydrogen,

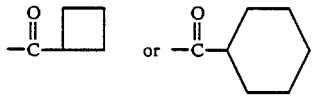

The present invention will now be described by the following examples, however the invention is not meant to be limited to the details therein.

EXAMPLE 1

1-[[[(S)-3-[[$N^2$-(Cyclobutylcarbonyl)-L-lysyl]-amino]-2-oxo-4-phenylbutyl]methyl-amino]carbonyl]-L-proline, 1.5 hydrochloride

A. $N^2$-(Cyclobutylcarbonyl)-$N^6$-[(phenylmethoxy)-carbonyl]-L-lysine $N^6$-[(Phenylmethoxy)carbonyl]-L-lysine (4.73 g, 16.9 mmole) was suspended in 50 ml of acetonitrile and thereafter bis(trimethylsilyl)trifluoroacetamide (18.5 ml, 17.92 g, 69.6 mmol) was added. After stirring the mixture for 45 minutes under argon, it became homogeneous. After cooling to 5° C., a solution of cyclobutane carboxylic acid chloride (2.02 g, 17 mmol) in 10 ml of tetrahydrofuran was added dropwise over 15 minutes. The reaction mixture was stirred for 2 hours and then partitioned between ethyl acetate and water. The ethyl acetate layer was concentrated to an oil, dissolved in a saturated bicarbonate solution and washed with ethyl acetate. The aqueous layer was acidified to pHz with concentrated hydrochloric acid and extracted with ethyl acetate. This ethyl acetate extract was dried over sodium sulfate and concentrated in vacuo to give the title A compound (5.46 g, 15.5 mmol).

B. (S)-[3-Chloro-2-oxo-1-(phenylmethyl)propyl]-carbamic acid, 1,1-dimethylethyl ester To a stirred solution of benzyloxy carbonyl-L-phenylalanine (26.5 g, 100 mmol) in tetrahydrofuran (150 ml) at −20° was added isobutylchloroformate (13 ml, 100 mmol). N-methylmorpholine (11 ml, 100 mmol) was then added in drops. The solution was stirred between −15° and −20° for fifteen minutes and was filtered. Tetrahydrofuran (25 ml) was used for the washings. This was added to a cold (ice bath) etheral solution of diazomethane in drops. After the addition was over, the ice bath was removed and the reaction mixture was stirred at ambient temperature for 2 hours. Nitrogen was blown over the solution and the volume was reduced to 400 ml. The reaction mixture was then stirred in an ice bath and hydrochloric acid in acetic acid (2N, 55 ml) was added in drops. After the addition was over, the ice bath was removed and the reaction mixture stirred for fifteen minutes at room temperature. The reaction mixture was evaporated in vacuo and the residue on attempted dissolution in ether afforded 6.2 g of the title B compound. The mother liquor on concentration and after crystallization from ether/hexane afforded another 17.65 g of the title B compound.

C. (S)-[3-[Methyl(phenylmethyl)amino]-2-oxo-1-(phenylmethyl)propyl]carbamic acid, 1,1-dimethylethyl ester, p-toluenesulfonate salt A solution of the compound of part B (6.45 g, 21.65 mmole), benzylmethylamine (2.78 ml, 21.55 mmole), $NaHCO_3$ (2.18 g, 26 mmole) and sodium iodide (1.62 g, 10.83 mmole) in dimethylformamide (75 ml) was stirred under argon at room temperature for 4 hours. The resulting mixture was concentrated in vacuo, diluted with ether, washed three times with water and extracted five times with 1N hydrochloric acid. The combined extracts were made basic using $NaHCO_3$ (solid) and extracted three times with ethyl acetate. The combined ethyl acetate extracts were dried over magnesium sulfate, concentrated and the residue was dissolved in ether. To this solution was added a warm solution of p-toluene-sulfonic acid (2.93 g, 15.4 mmole) in ethyl acetate. The resulting orange solution was seeded with product crystals from an earlier run and cooled until crystallization was complete. The resulting crystalline solid was collected and washed with ether to give the title C compound (7.43 g, 13.40 mmole).

D. (S)-[3-(Methylamino)-2-oxo-1-(phenylmethyl)-propyl]-carbamic acid, 1,1-dimethylethyl ester, p-toluenesulfonate(1:1)salt A solution of the compound of part C (7.33 g, 13.2 mmole) and palladium dihydroxide in methanol was stirred under a positive pressure of hydrogen for 3 hours. The resulting solution was filtered and concentrated. The product was crystallized from ether to give the title D compound (5.82 g, 12.53 mmole).

E. (S)-1-[[[3-[[(1,1-Dimethylethoxy)carbonyl]-amino]-2-oxo-4-phenylbutyl]methylamino]-carbonyl]-L-proline, phenylmethyl ester To a stirring solution of L-proline benzyl ester hydrochloride (6.05 g, 25 mmole) in methylene chloride (100 ml) at −30° C. were added N-methyl morpholine (6.9 ml, 62.5 mmole) and phosgene (40 ml, 48 mmole, 12 percent in benzene). The resulting solution was stirred at −30° for one hour and at room temperature for an additional hour. The mixture was concentrated at reduced pressure and to the residue was added methylene chloride (60 ml), a solution of the compound of part D (7.75 g, 16.68 mmole) in methylene chloride (100 ml) and N-methyl morpholine (5.5 ml, 50 mmole). The resulting mixture was stirred at room temperature overnight and concentrated. The residue was dissolved in ethyl acetate, washed with water, 1N hydrochloric acid, and 10 percent $NaHCO_3$, dried over magnesium sulfate and concentrated to an orange oil. The crude product was chromatographed on silica gel. Fractions containing the desired product were combined and concentrated to give the title E compound as a beige foam (7.17 g, 13.7 mmole).

F (S)-1-[[(3-Amino-2-oxo-4-phenylbutyl)methylamino]-carbonyl]-L-proline, phenylmethyl ester, monohydrochloride A solution of the compound of part E (7.12 g, 13.6 mmole) was stirred in a saturated solution of hydrochloric acid/ethyl acetate for one hour. The resulting precipitate was collected and washed with ethyl acetate to give the title F compound.

G.

1-[[[(S)-3-$N^2$-(Cyclobutylcarbonyl)-$N^6$-[(phenylmethoxy)carbonyl]-L-lysyl]amino]-2-oxo-4-phenylbutyl]-methylamino]carbonyl]-L-proline phenylmethyl ester, 1.5 hydrochloride To a solution of the compound of part A (0.54 g, 1.5 mmol) in 20 ml of dimethylformamide −50° C. and under nitrogen was added triethylamine (0.21 ml, 1.5 mmol) and isobutylchloroformate (0.19 ml, 1.5 mmol). After 20 minutes of stirring at −50° C. a solution of the compound of part F (0.69 g, 1.5 mmol) in 10 ml of dimethylformamide was added, followed quickly by the addition of diisopropylethyl amine (0.26 ml, 1.5 mmol). The internal temperature rose to −35° C. After stirring overnight (from −35° C. to room temperature) the reaction mixture was poured into 100 ml of water and extracted three times with ethyl acetate. The combined ethyl acetate extracts were washed twice with saturated sodium hydrogen carbonate, twice with 10 percent potassium hydrogen sulfate, twice with water and dried over magnesium sulfate. The so-treated extracts were thereafter concentrated under reduced pressure to give a yellow oil. Purification by flash chromatography and recrystallization from ethyl acetate/hexane afforded the title G compound as white crystals (0.49 g).

H.

1-[[[(S)-3-[[$N^2$-(Cyclobutylcarbonyl)-L-lysyl]-amino]-2-oxo-4-phenylbutyl]methylamino]carbonyl]-L-proline, 1.5 hydrochloride A solution of the compound of part G (0.25 g, 0.32 mmol) in 50 ml of ethanol containing 1N hydrochloric acid (0.64 ml, 0.64 mmol) and 10 percent palladium on carbon was hydrogenated overnight. The reaction mixture was filtered and the filtrate was concentrated. The solid residue was triturated with ether and the product was lyophilized in double distilled water two times affording the title compound as a fluffy white solid (0.14 g).

EXAMPLE 2

1-[[[(S)-3-[[N'-(Cyclobutylcarbonyl)-L-lysyl]-amino]-2-hydroxy-4-phenylbutyl]methylamino]carbonyl]-L-proline, 1.5 hydrochloride

A.

1-[[[(S)-3-[[$N^2$-(Cyclobutylcarbonyl)-$N^6$-[(phenylmethoxy)carbonyl]-L-lysyl]-amino]-2-hydroxy-4-phenylbutyl]methylamino]carbonyl]L-proline phenylmethyl ester, 1.5 hydrochloride A sample of the compound from part G of Example 1 was dissolved in ethanol (15 ml). While stirring in an ice bath, sodium borohydride (150 mg, 3.95 mmol) was added. The solution was stirred at room temperature for 90 minutes. It was then evaporated, taken into ethyl acetate and washed with 10 percent aqueous potassium hydrogen sulfate solution. The ethyl acetate solution (after evaporation) was chromatographed over silica gel to obtain 1.1 grams of the title A compound.

B 1-[[[(S)-3-[[$N^2$-(Cyclobutylcarbo 1)-L-lysyl-]-amino]-2-hydroxy-4-phenylbutyl]-methylamino]carbonyl]-L-proline, 1.5 hydrochloride The compound from part A of this Example was thereafter treated using the procedures of part H in Example 1 to obtain the title compound.

EXAMPLES 3–30

Using the methods and procedures described above and in Examples 1 and 2, the following additional compounds of the present invention can be made.

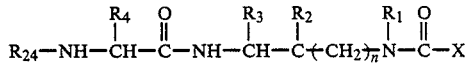

| Ex. | $R_{24}$ | $R_4$ | $R_3$ | $R_2$ | n | $R_1$ | X |
|---|---|---|---|---|---|---|---|
| 3 | 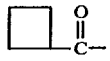 | —H | —$C_4H_9$ | O ‖ | one | —$CH_3$ | 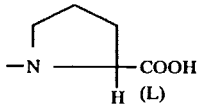 |
| 4 | 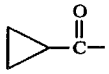 | —$(CH_2)_4$—$NH_2$ | 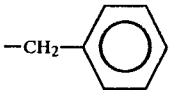 | O ‖ | one | —$CH_3$ | 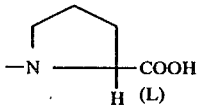 |
| 5 | 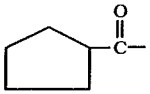 | —$(CH_2)_4$—$NH_2$ | 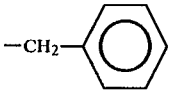 | —OH | one | —$C_2H_5$ | 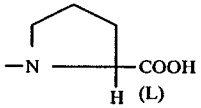 |
| 6 | 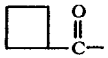 | —$(CH_2)_4$—$NH_2$ | —$C_4H_9$ | O ‖ | two | —$CH_3$ | 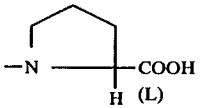 |
| 7 | 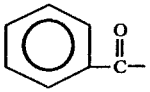 | —$(CH_2)_4$—$NH_2$ | 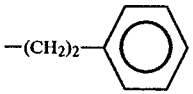 | O ‖ | one | —$(CH_2)_4$—$NH_2$ | 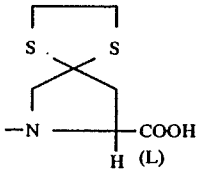 |
| 8 | 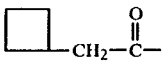 | —$CH_3$ | —$C_4H_9$ | —OH | one | —$(CH_2)_3$—$NH_2$ | 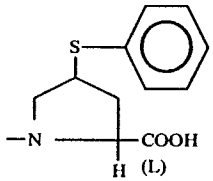 |

-continued
| Ex. | $R_{24}$ | $R_4$ | $R_3$ | $R_2$ | n | $R_1$ | X |
|---|---|---|---|---|---|---|---|
| 9 | 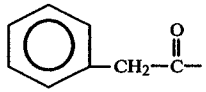 | 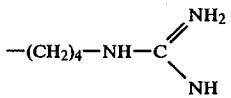 | 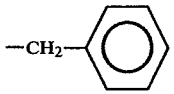 | O ‖ | two | 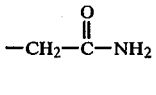 | 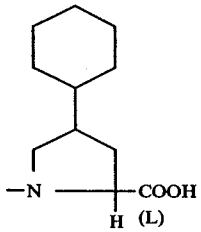 |
| 10 | 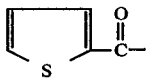 | $-(CH_2)_5-NH_2$ | $-C_4H_9$ | O ‖ | one | $-CH_3$ | 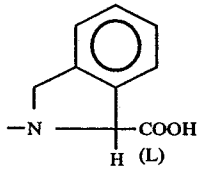 |
| 11 | 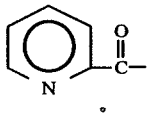 | $-(CH_2)_4-NH_2$ | $-C_4H_9$ | O ‖ | one | $-CH_3$ | 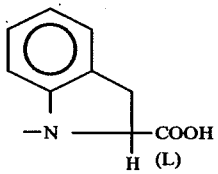 |
| 12 | 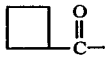 | 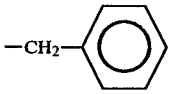 | 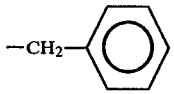 | $-OH$ | one | $-CH_3$ | 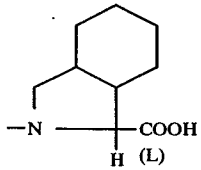 |
| 13 | 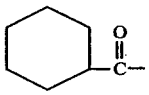 | $-(CH_2)_4-NH_2$ | 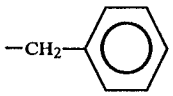 | O ‖ | one | $-CH_3$ | 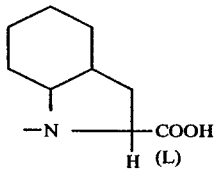 |

-continued
| Ex. | $R_{24}$ | $R_4$ | $R_3$ | $R_2$ | n | $R_1$ | X |
|---|---|---|---|---|---|---|---|
| 14 | 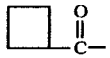 | $-(CH_2)_4-NH_2$ | 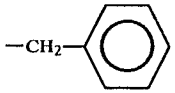 | O | two | $-CH_3$ | 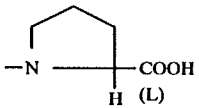 |
| 15 | 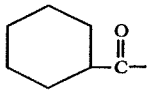 | $-(CH_2)_4-NH_2$ | $-C_3H_7$ | O | one | $-CH_3$ | 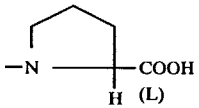 |
| 16 | $-H$ | $-(CH_2)_4-NH_2$ | $-C_4H_9$ | O | one | $-CH_3$ | $-NH-CH_2-COOH$ |
| 17 | 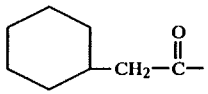 | $-CH_3$ | 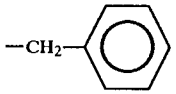 | $-OH$ | two | $-(CH_2)_4-NH_2$ | 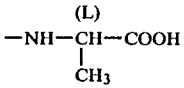 |
| 18 | 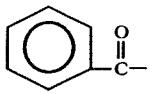 | $-CH_2-S-CH_3$ | $-C_4H_9$ | O | one | $-(CH_2)_4-NH_2$ | 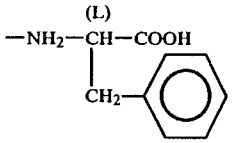 |
| 19 | 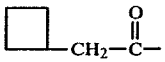 | 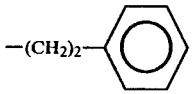 | $-CH_3$ | O | one | $-(CH_2)_3-NH_2$ | 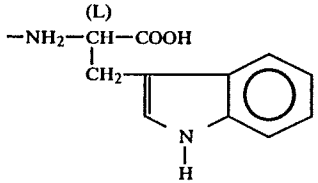 |
| 20 | 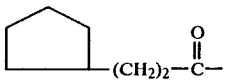 | $-CH_3$ | $-C_4H_9$ | O | one | $-(CH_2)_2-OH$ | 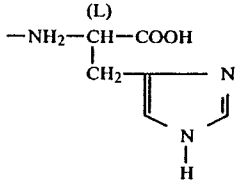 |

-continued
| Ex. | $R_{24}$ | $R_4$ | $R_3$ | $R_2$ | n | $R_1$ | X |
|---|---|---|---|---|---|---|---|
| 21 | 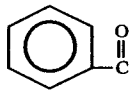 | $-(CH_2)_4-NH_2$ | $-C_2H_5$ | O ‖ | one | $-CH_3$ | 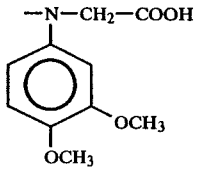 |
| 22 | 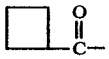 | $-(CH_2)_4-NH_2$ | $-C_2H_9$ | O ‖ | one | $-CH_3$ | 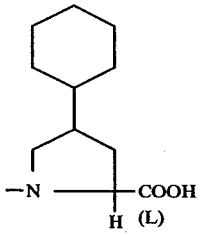 |
| 23 | 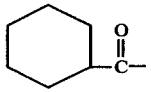 | $-(CH_2)_4-NH_2$ | 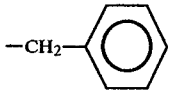 | O ‖ | two | $-CH_3$ | 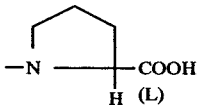 |
| 24 | 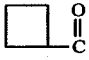 | $-(CH_2)_3-CH_3$ | 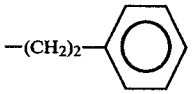 | $-OH$ | one | $-CH_3$ | 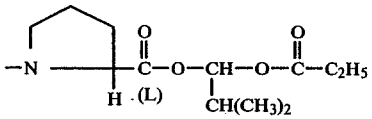 |
| 25 | 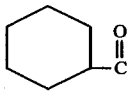 | $-(CH_2)_3-CH_3$ | 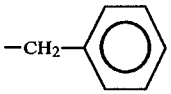 | O ‖ | one | $-CH_3$ | 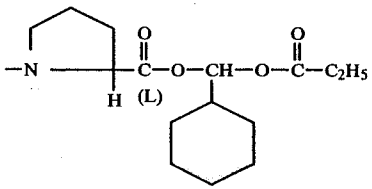 |
| 26 | H— | $-CH_3$ | 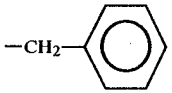 | O ‖ | one | $-(CH_2)_4-NH_2$ | 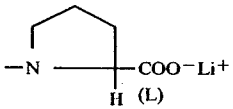 |

-continued
| Ex. | $R_{24}$ | $R_4$ | $R_3$ | $R_2$ | n | $R_1$ | X |
|---|---|---|---|---|---|---|---|
| 27 | H— | —$(CH_2)_3$—$CH_3$ | 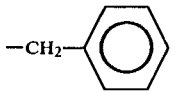 | O ‖ | one | —$CH_3$ | 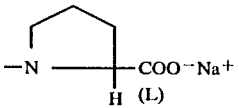 |
| 28 | H— | —$CH_3$ | 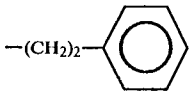 | O ‖ | one | —$CH_3$ | 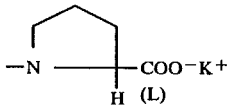 |
| 29 | H— | —$(CH_2)_3$—$CH_3$ | 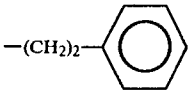 | O ‖ | one | —$CH_3$ | 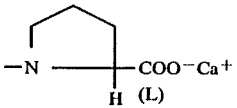 |
| 30 | 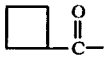 | —$CH_3$ | 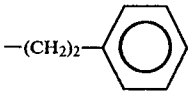 | O ‖ | one | —$CH_3$ | 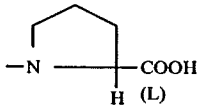 |

What is claimed is:

1. A compound of the formula

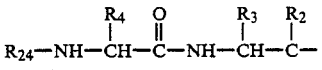

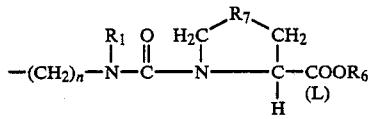

or a pharmaceutically acceptable salt thereof wherein $R_1$ is hydrogen, lower alkyl,

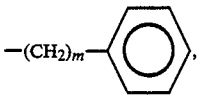

—$(CH_2)_m$-cycloalkyl, —$(CH_2)_2$—$NH_2$, —$(CH_2)_3$—$NH_2$, —$(CH_2)_4$—$NH_2$;

n is one or two;

$R_2$ is

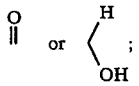

$R_3$ and $R_4$ are independently selected from hydrogen, lower alkyl,

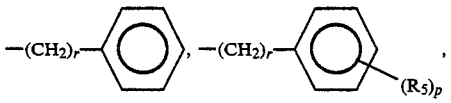

—$(CH_2)_r$—cycloalkyl, —$(CH_2)_r$—$NH_2$, $CF_3$,

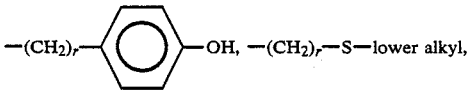

—$(CH_2)_r$—NH—C(=NH)—$NH_2$, or —$(CH_2)_r$—C(=O)—$NH_2$;

$R_{24}$ is hydrogen,

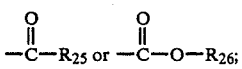

$R_{25}$ is hydrogen, lower alkyl,

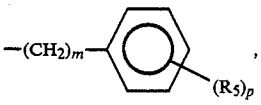

—$(CH_2)_m$-cycloalkyl, or

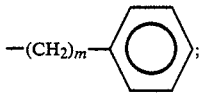

$R_{26}$ is lower alkyl, —$(CH_2)_q$-cycloalkyl,

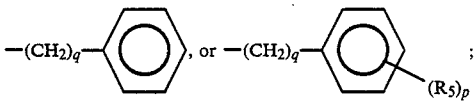

m is zero or an integer from 1 to 4, r is an integer from 1 to 7, q is an integer from 1 to 4, $R_7$ is hydrogen or lower alkyl;

$R_5$ is lower alkyl of 1 to 4 carbons, lower alkoxy of 1 to 4 carbons, lower alkylthio of 1 to 4 carbons, chloro, bromo, fluoro, trifluoromethyl or hydroxy, $R_6$ is hydrogen, lower alkyl, benzyl, benzhydryl, alkali metal salt ion, alkaline earth metal salt ion

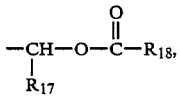

or —$(CH_2)_2Si(CH_3)_3$; and p is one, two or three provided that p is more than one only if Rs is methyl, methoxy, chloro, bromo or fluoro.

2. A compound of claim 1 wherein n is one;

$R_1$ is —$CH_3$ or —$(CH_2)_4$—$NH_2$;

$R_2$ is

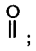

$R_3$ is

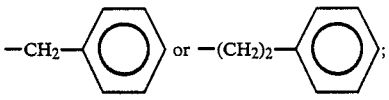

$R_4$ is methyl, n-butyl, or —$(CH_2)_4$—$NH_2$, and $R_{24}$ is hydrogen,

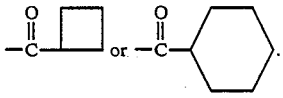

3. The compound of claim 1 wherein $R_1$ is methyl;

$R_2$ is

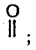

$R_3$ is

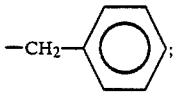

$R_4$ is $—CH_2)_4—NH_2$
$R_6$ is hydrogen; and
$R_{24}$ is

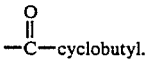

4. The compound of claim 1 having the name 1-[[[(S)-3-[[$N^2$-(cyclobutylcarbonyl)-L-lysyl]-amino-2-oxo-4-phenylbutylmethylamino]carbonyl]-L-proline, 1.5 hydrochloride.

5. The compound of claim 1 wherein
$R_1$ is methyl;
$R_2$ is

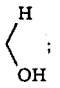

$R_3$ is

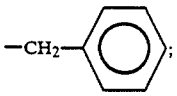

$R_4$ is $—(CH_2)_4—NH_2$;
$R_6$ is hydrogen;
$R_{24}$ is

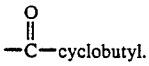

6. The compound of claim 1 having the name 1-[[[(S)-3-[[$N^2$-(Cyclobutylcarbonyl)-L-lysyl]-amino-2-hydroxy-4-phenylbutyl]methylamino]carbonyl]-L-proline, 1.5 hydrochloride.

* * * * *